United States Patent
Miller et al.

(10) Patent No.: US 7,608,641 B2
(45) Date of Patent: *Oct. 27, 2009

(54) CREATINE ORAL SUPPLEMENTATION USING CREATINE HYDROCHLORIDE SALT

(75) Inventors: Donald W. Miller, Winnipeg (CA); Jonathan L. Vennerstrom, Omaha, NE (US); Mark C. Faulkner, Madison, TN (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 888 days.

This patent is subject to a terminal disclaimer.

(21) Appl. No.: 10/846,782

(22) Filed: May 14, 2004

(65) Prior Publication Data

US 2004/0242691 A1    Dec. 2, 2004

Related U.S. Application Data

(60) Provisional application No. 60/470,356, filed on May 15, 2003.

(51) Int. Cl.
*A61K 31/195*    (2006.01)

(52) U.S. Cl. .................................................. 514/565
(58) Field of Classification Search ............... 514/565
See application file for complete search history.

(56) References Cited

U.S. PATENT DOCUMENTS

| | | | |
|---|---|---|---|
| 5,817,329 | A | 10/1998 | Gardiner |
| 6,136,339 | A | 10/2000 | Gardiner |
| 6,620,425 | B1 | 9/2003 | Gardiner |
| 6,784,209 | B1 | 8/2004 | Gardiner et al. |
| 6,897,334 | B2 * | 5/2005 | Vennerstrom ............... 560/169 |

FOREIGN PATENT DOCUMENTS

WO    0222135    3/2002

* cited by examiner

*Primary Examiner*—Kevin Weddington
(74) *Attorney, Agent, or Firm*—Hanify & King, P.C.

(57) ABSTRACT

Creatine oral supplementation using creatine hydrochloride salt, that may be added to a liquid or other beverage, or may be also used as an additive to solid oral dosages, or as a supplement, and which may be consumed by the athlete, or other party looking for immediate supplementation of strength, and may be added as a supplement within feed to livestock, in the veterinary area.

7 Claims, No Drawings

CREATINE ORAL SUPPLEMENTATION USING CREATINE HYDROCHLORIDE SALT

CROSS REFERENCE TO RELATED APPLICATION

This non-provisional patent application claims priority to the provisional application for patent having Ser. No. 60/470,356, which was filed on May 15, 2003.

BACKGROUND OF THE INVENTION

Dietary supplementation with creatine is an approved and accepted means for increasing muscle performance, and increasing muscle mass. Most current commercial applications involving creatine supplementation use the creatine monohydrate form as the primary embodiment. A limitation of creatine supplements using the creatine monohydrate form is that the products have low aqueous solubility and require relatively large doses of creatine be consumed with large amounts of fluid. The physiochemical properties of creatine monohydrate are such that oral absorption is limited. There are other salt forms including creatine citrate (creatine effervescent) and creatine pyruvate that have been patented and marketed as improvements over creatine monohydrate. Despite the various salt forms currently marketed, there is an unmet need for an improved form of creatine that could be taken in a more convenient dosage form and have better oral absorption characteristics.

SUMMARY OF THE INVENTION

This invention relates principally to the use of creatine hydrochloride salt for application to aqueous solutions for use as a beverage in the sports environment, liquid meal replacement, nutritional energy bars, and other fortified foods.

In essence, this invention relates to the usage of a granular precipitate consisting of creatine hydrochloride salt in a high purity and yield. More specifically, the creatine hydrochloride salt, when added to a solution, and used as a beverage or other form of drink, functions as a nutritional supplement for enhancing muscle performance and developing muscle mass in both humans and livestock.

It is, therefore, the principle object of this invention to utilize creatine hydrochloride salt, apart from other forms of creatine, but in this instance, having high aqueous solubility so as to readily mix with any liquid, or beverage, and having application in the field of athletics to enhance developed and generated strength.

Another object of this invention is the application of hydrochloride salts, of creatine form, that may be added as a feed additive when fed to livestock, or other animals.

These and other objects may become more apparent to those skilled in the art upon review of the summary of the invention as provided herein and upon undertaking a study of the description of its preferred embodiment.

DESCRIPTION OF THE PREFERRED EMBODIMENT

The present invention involves a process for the production of the hydrochloride salt form of creatine. The process uses creatine monohydrate and acetyl chloride as the reactants and, ethanol as the preferred solvent. The product of this reaction is a granular precipitate consisting of the creatine hydrochloride salt in high purity and yield.

The invention also involves an application or use of the creatine hydrochloride salt as a nutritional supplement for enhancing muscle performance and muscle mass in both humans and livestock. What sets this creatine hydrochloride salt apart from the other forms of creatine is its high aqueous solubility. Studies in the inventors' laboratory indicate that the aqueous solubility of the creatine hydrochloride is 150 mg/ml or greater, while that of creatine monohydrate and creatine citrate salt is at least an order of magnitude lower (approximately 10-15 mg/ml). As the low oral absorption of creatine supplements are believed to be attributable in part to reduced solubility, the creatine hydrochloride would be expected to have better oral absorption properties. An alternate embodiment of the process uses anhydrous creatine. An alternate embodiment of the process uses other short chain alcohols selected from methanol, propanol, butanol, isopropanol, among others to replace the ethanol solvent.

Various other applications for use with this type of a salt, other than in the sports beverage area, may include its application as a feed additive in livestock. Certainly, based upon what is now known about the product, it would have immediate applications in the solid oral dosage supplementation area, as an additive or a feed supplement in livestock feed. Or, it may be added into a liquid, or any water, that is fed to the livestock, during there consumption of liquids and solids.

This is contemplated within the essence of this invention that the formulation for the oral supplementation of this invention could be provided in a solid oral dosage form, such as in a capsule form, or tablets, for treatment requirements when taken by the human, animal, and the like. This is known in the art. The formulation for the creatine oral supplementation, using the Creatine Hydrochloride Salt, is CrHCl. The formulation could be added into a beverage in addition the CrHCl may be provided as an ingredient to a sports drink, liquid meal replacement, or the like, and as can be understood. Furthermore, the concept of this invention for use of this formulation within a supplementation can be used and applied for nutritional and energy purposes. Furthermore, the composition could be added as a fortification to other foods. Finally, it is likely that this composition could be added as a feed supplement, to further enhance the energy requirements of the horses, and other animals, as may be desired and required.

The product of this reaction of creatine monohydrate and acetyl chloride dissolved in ethanol is a granular precipitate consisting of the creatine hydrochloride salt in high purity and yield. Yield is measured by 1H-NMR analysis used for organic chemicals. 1H-NMR uses spectroscopy and nuclear magnetic resonance technology to ascertain the structure of chemical compounds.

The reactants are measured as mole equivalents while the solvent is measured as milliliters per gram of creatine hydrochloride salt. The preferred process uses 1.4 mole equivalents of acetyl chloride. Above 1.5 and including 2.0 mole equivalents acetyl chloride, the process produces less desirable creatine ethyl ester hydrochloride at a sacrifice of yield for creatine hydrochloride. Above 2.0 mole equivalents acetyl chloride, the process forms creatinine hydrochloride. The preferred process dissolves the reactants in 10 ml of ethanol. Alternatively, the process has ethanol ranging from about 6 to about 10 ml. The preferred process operates in a temperature range of 25 deg. C. to 35 deg. C. At temperatures above the preferred range including 50 deg. C., the process produces the less desirable creatine ethyl ester hydrochloride. In excess of 50 deg. C., the process produces creatinine hydrochloride.

However, even in the preferred embodiment minor fractions of creatine ethyl ester hydrochloride and creatinine hydrochloride are produced.

To form creatine hydrochloride salt, a manufacturer blends creatine monohydrate with acetyl chloride in a vessel. Then ethanol is added to the vessel as a solvent. The temperature of the solution is raised to between about 24 deg. C. to about 50 deg. C., preferably to 25 deg. C. In that condition, the solution precipitates a hydrochloride salt of creatine in granular form in the vessel. After reducing the temperature and pressure to ambient atmospheric temperature and pressure, the manufacturer collects the granules of creatine hydrochloride salt then packages the granules for consumption by humans or livestock.

As an alternative method, a manufacturer produces creatine hydrochloride by bubbling gaseous HCl into diethyl ether solvent. Then, creatine monohydrate is stirred into the solvent. From the reaction, creatine hydrochloride precipitates. The manufacturer then filters and washes the precipitate. Lastly, the precipitate dries at room temperature to a crystalline form, white in color and then is packaged for human or livestock consumption. In using the alternative method, the HCl may have a range of concentrations so long as the HCl exceeds the molar equivalent of creatine monohydrate. Next, the alternative method stirred from about 0 grams to about 5 grams of creatine monohydrate into the solution at 25 deg. C. for two hours. Filtering and washing were performed with 50 milliliters of fresh diethyl ether.

Variations or modifications to the subject matter may occur to those skilled in the art upon review of the invention as described herein. Such variations, if within the spirit of this development, are intended to be encompassed within the scope of the invention as defined herein. The description of the preferred embodiment, as provided, is set forth for illustrative purposes only.

We claim:

1. A supplement to increase muscle mass and muscle performance consisting of creatine hydrochloride salt formed from the reaction product of:
    about 0.8 to about 1.2 mole equivalent creatine monohydrate; and
    about 1.1 to about 1.4 mole equivalents acetyl chloride, dissolved in about 6 to about 10 milliliters alcohol solution per gram of creatine hydrochloride salt at a temperature of about 25° C. to about 35° C.,
    wherein the supplement has an aqueous solubility of at least 150 mg/ml.

2. The supplement of claim 1, wherein the reaction product is formed from:
    about 1 mole equivalent creatine monohydrate; and
    about 1.4 mole equivalents acetyl chloride dissolved in about 10 milliliters ethanol solution.

3. The supplement of claim 2, wherein the supplement is precipitated as granules and then packaged into an oral dosage form.

4. The supplement of claim 1, wherein the supplement has an aqueous solubility of at least an order of magnitude higher than the aqueous solubility of creatine monohydrate.

5. The supplement of claim 1, wherein the yield of creatine hydrochloride salt is approximately 94 percent.

6. A supplement for to increase muscle mass and muscle performance consisting of creatine hydrochloride salt formed from the reaction product of:
    about 1 mole equivalent creatine monohydrate:
    about 1.4 mole equivalents acetyl chloride;
    said creatine monohydrate and said acetyl chloride dissolving in about 10 milliliters ethanol solution at a temperature of about 25° C. forming a solution of creatine hydrochloride having an aqueous solubility of at least 150 mg/ml; and
    thus precipitating granules of creatine hydrochloride salt from the solution for oral dosage as one pill, capsule, tablet, or liquid.

7. The supplement of claim 6, wherein the yield of creatine hydrochloride salt is approximately 94 percent.

* * * * *